United States Patent
Moskal

(10) Patent No.: US 10,088,581 B2
(45) Date of Patent: Oct. 2, 2018

(54) METHOD AND A SYSTEM FOR DETERMINING PARAMETERS OF REACTIONS OF GAMMA QUANTA WITHIN SCINTILLATION DETECTORS OF PET SCANNERS

(71) Applicant: UNIWERSYTET JAGIELLONSKI, Crakow (PL)

(72) Inventor: Pawel Moskal, Czulowek (PL)

(73) Assignee: UNIWERSYTET JAGIELLONSKI, Krakow (PL)

( * ) Notice: Subject to any disclaimer, the term of this patent is extended or adjusted under 35 U.S.C. 154(b) by 136 days.

(21) Appl. No.: 14/915,252

(22) PCT Filed: Aug. 29, 2014

(86) PCT No.: PCT/EP2014/068355
§ 371 (c)(1),
(2) Date: Feb. 29, 2016

(87) PCT Pub. No.: WO2015/028596
PCT Pub. Date: Mar. 5, 2015

(65) Prior Publication Data
US 2016/0209523 A1    Jul. 21, 2016

(30) Foreign Application Priority Data

Aug. 30, 2013  (PL) ........................... 405179

(51) Int. Cl.
*G01T 1/29*   (2006.01)
*A61B 6/03*   (2006.01)
*G01T 1/20*   (2006.01)

(52) U.S. Cl.
CPC ............ *G01T 1/2985* (2013.01); *A61B 6/037* (2013.01); *G01T 1/20* (2013.01)

(58) Field of Classification Search
CPC .......... G01T 1/20; G01T 1/2985; A61B 6/037
See application file for complete search history.

(56) References Cited

U.S. PATENT DOCUMENTS 6,459,085 B1 * 10/2002 Chang ................... G01T 1/1642
                                                        250/367
2013/0256536 A1 * 10/2013 Kim ...................... G01T 1/1648
                                                        250/362

FOREIGN PATENT DOCUMENTS

WO    WO2012130335 A1 * 10/2012

* cited by examiner

*Primary Examiner* — Evren Seven
(74) *Attorney, Agent, or Firm* — Mark M. Friedman

(57) ABSTRACT

A method for determining parameters of reaction of a gamma quantum within a scintillation detector of a PET scanner, wherein the signal measured by the scintillator is transformed in at least one photomultiplier into an electric measured signal. The method comprises obtaining an access to a database (130) comprising reference standard signals (W) and reaction parameters assigned to the reference standard signals (W); comparing the measured signal (S) to the reference standard signals (W) and selecting the reference standard signal (W) that best fits the measured signal (S); assigning to the measured signal (S) the reaction parameters assigned to the selected best-fitting reference standard signal (W), as parameters of the reaction of the gamma quantum within the scintillation detector (101) for the measured signal (S); wherein the measured signal (S) and the reference standard signals (W) are represented by points (P) within a generalized measurement space ($\Omega p$) having a number of dimensions (N measurements) being equal to the total number of measurements performed for that gamma quantum.

10 Claims, 2 Drawing Sheets

METHOD AND A SYSTEM FOR DETERMINING PARAMETERS OF REACTIONS OF GAMMA QUANTA WITHIN SCINTILLATION DETECTORS OF PET SCANNERS

TECHNICAL FIELD

The disclosure relates to a method and a system for determining the parameters of the reactions of gamma quanta within scintillation detectors of PET scanners.

BACKGROUND

Images of the interiors of bodies may be acquired using various types of tomographic techniques, which involve recording and measuring radiation from tissues and processing acquired data into images.

One of these tomographic techniques is positron emission tomography (PET), which involves determining spatial distribution of a selected substance throughout the body and facilitates detection of changes in the concentration of that substance over time, thus allowing to determine the metabolic rates in tissue cells.

The selected substance is a radiopharmaceutical administered to the examined object (e.g. a patient) before the PET scan. The radiopharmaceutical, also referred to as an isotopic tracer, is a chemical substance having at least one atom replaced by a radioactive isotope, e.g. $^{11}C$, $^{15}O$, $^{13}N$, $^{18}F$, selected so that it undergoes radioactive decay including the emission of a positron (antielectron). The positron is emitted from the atom nucleus and penetrates into the object's tissue, where it is annihilated in reaction with an electron present within the object's body.

The phenomenon of positron and electron annihilation, constituting the principle of PET imaging, consists in converting the masses of both particles into energy emitted as annihilation photons, each having the energy of 511 keV. A single annihilation event usually leads to formation of two photons that diverge in opposite directions at the angle of 180° in accordance with the law of conservation of the momentum within the electron-positron pair's rest frame, with the straight line of photon emission being referred to as the line of response (LOR). The stream of photons generated in the above process is referred to as gamma radiation and each photon is referred to as gamma quantum to highlight the nuclear origin of this radiation. The gamma quanta are capable of penetrating matter, including tissues of living organisms, facilitating their detection at certain distance from object's body. The process of annihilation of the positron-electron pair usually occurs at a distance of several millimeters from the place of the radioactive decay of the isotopic tracer. This distance constitutes a natural limitation of the spatial resolution of PET images to a few milimeters.

A PET scanner comprises detection devices used to detect gamma radiation as well as electronic hardware and software allowing to determine the position of the positron-electron pair annihilation event on the basis of the position and time of detection of a particular pair of the gamma quanta. The radiation detectors are usually arranged in layers forming a ring around object's body and are mainly made of an inorganic scintillation material. A gamma quantum enters the scintillator, which absorbs its energy to re-emit it in the form of light (a stream of photons). The mechanism of gamma quantum energy absorption within the scintillator may be of dual nature, occurring either by means of the Compton's effect or by means of the photoelectric phenomenon, with only the photoelectric phenomenon being taken into account in calculations carried out by current PET scanners. Thus, it is assumed that the number of photons generated in the scintillator material is proportional to the energy of gamma quanta deposited within the scintillator.

When two annihilation gamma quanta are detected by a pair of detectors at a time interval not larger than several nanoseconds, i.e. in coincidence, the position of annihilation position along the line of response may be determined, i.e. along the line connecting the detector centers or the positions within the scintillator strips where the energy of the gamma quanta was deposited. The coordinates of annihilation place are obtained from the difference in times of arrival of two gamma quanta to the detectors located at both ends of the LOR. In the prior art literature, this technique is referred to as the time of flight (TOF) technique and the PET scanners utilizing time measurements are referred to as TOF-PET scanners. This technique requires that the scintillator has a time resolution of a few hundred picoseconds.

Currently, the state of the art methods of determining the sites of interactions of the gamma quanta in positron emission tomography are based on the measurements of charges of signals generated in vacuum tube photomultipliers, silicon photomultipliers, or avalanche diodes optically connected to inorganic crystals notched into smaller elements. Position of the gamma quantum reaction is determined with the accuracy of the size of a smaller crystal element on the basis of the differences in charges of the signals from different converters optically connected to the same crystal. In the state of the art PET scanners, reconstruction of the set of LOR and TOF data is based on the relationships between charges and times of signals recorded for a particular event without reference to external reference signals.

In the signal time determination methods used in the state of the art, changes in shapes and amplitudes of signals depending on the place of ionization and the quantity of energy constitute a limitation in temporal resolutions that can be achieved using the technique. The larger the scintillator, the larger the variations in signal shapes and amplitudes.

For the above reasons, temporal resolutions of less than 100 ps are unattainable in the state of the art for large scintillator blocks. Temporal resolution also translates on the resolution of ionization place determination. In case of polymer scintillators (preferred due to their low price), amplitudes of signals generated by the gamma quanta, including annihilation gamma quanta used in positron emission tomography, are characterized by continuous distribution resulting from interactions between gamma quanta and electrons occurring mostly via the Compton effect with a negligibly low probability of a photoelectric effect. As a consequence, signal amplitudes in polymer scintillators may change even if they originate from the same place.

As shown by the shortcomings of the state of the art signal analysis techniques, there is a need to significantly improve temporal and spatial resolution in the detectors used in medical diagnostic techniques that require recording of ionizing radiation. The need to improve resolution is particularly high in large-sized detectors. Examples of PET detectors making use of large polymeric scintillators were described in the PCT application WO 2011/008119 as well as in the PCT application WO 2011/008118. Solutions described in these applications are based on the measurements of the times of light pulses arrival to the detector edges. Light pulses are converted into electric pulses by means of photomultipliers. The shape (distribution of photons as a function of time) and the amplitude of the light pulse reaching the photomultiplier varies depending on the distance between the photomultiplier and the pulse origin place. In addition and independently of the ionization place, the amplitude of the signal varies with the energy deposited within the detector. As a consequence, due to variations in signal shapes and amplitudes, it is impossible to achieve good temporal resolution using either leading edge or constant fraction discriminators used in state of the art, due to the time walk effect and the pulse shape change effect observed in large-size scintillators.

The goal of this invention is to develop a method for reconstructing the place of the reaction of gamma quanta in PET detectors as well as for reconstructing the difference between the times of flight (TOF) of the annihilation quanta to different detectors such that said method would not deteriorate spatial or temporal resolution capabilities even in cases when the times of arrival and the shapes of the recorded pulses would vary greatly depending on the place of reaction of a particular gamma quantum within the detector.

SUMMARY

There is presented a method for determining parameters of reaction of a gamma quantum within a scintillation detector of a PET scanner, wherein the signal measured by the scintillator is transformed in at least one photomultiplier into an electric measured signal. The method comprises obtaining an access to a database comprising reference standard signals (W) and reaction parameters assigned to the reference standard signals (W); comparing the measured signal (S) to the reference standard signals (W) and selecting the reference standard signal (W) that best fits the measured signal (S); assigning to the measured signal (S) the reaction parameters assigned to the selected best-fitting reference standard signal (W), as parameters of the reaction of the gamma quantum within the scintillation detector for the measured signal (S). The measured signal (S) and the reference standard signals (W) are represented by points (P) within a generalized measurement space ($\Omega p$) having a number of dimensions ($N_{measurements}$) being equal to the total number of measurements performed for that gamma quantum.

Preferably, coordinates of the points (P) are ordered and correspond to crossing times when the signals (S, W) cross threshold voltages, measured using discriminators and/or amplitudes or charges of the signals (S, W).

Preferably, the generalized measurement space ($\Omega p$) comprises dimensions of time measurements ($N_f$) carried out by means of a constant fraction discriminator for the rising edge of the signal (S, W), as well as dimensions of time measurements for the rising edge ($N_{sr}$) and for the falling edge ($N_{sf}$) of the signal (S, W) measured by a leading edge discriminator.

Preferably, a total of $N_f + N_{sr} + N_{sf}$ time measurements are carried out with respect to a trigger signal.

Preferably, the reference standard signals (W) are generated using a collimated beam of gamma quanta.

Preferably, each of the reference standard signals (W) in the database is assigned information on a place of incidence of the collimated beam of gamma quanta onto the scintillation detector.

Preferably, the reference standard signals (W) contained in the database are synchronized such that for each of the reference standard signals (W) the time corresponding to the reaction of the gamma quantum within the scintillation detector is the same, preferably equal to zero.

Preferably, the reference standard signal (W) that best fits the measured signal (S) is selected by minimizing distances between points representing the signals (S, W) being compared within the measurement space as a function of the relative times between the compared signals (S, W).

Preferably, the method further comprises determining a time of flight as a difference in time between the measured signals (S) and the best-fitting reference standard signals (W).

There is also presented a system for determining parameters of reaction of a gamma quantum within a scintillation detector of a PET scanner wherein the signal measured by the scintillator is transformed in at least one photomultiplier into an electric measured signal. The system comprises a database comprising reference standard signals (W) and reaction parameters assigned to the reference standard signals (W); a comparator configured to compare the measured signal (S) with the reference standard signals (W) and to select the reference standard signal that best fits the measured signal (S); wherein the measured signal (S) and the reference standard signals (W) are represented by points (P) within a generalized measurement space (Op) having a number of dimensions ($N_{measurements}$) being equal to the total number of measurements performed for that gamma quantum.

BRIEF DESCRIPTION OF FIGURES

Example embodiments are presented on a drawing wherein.

DETAILED DESCRIPTION

Figure 3:
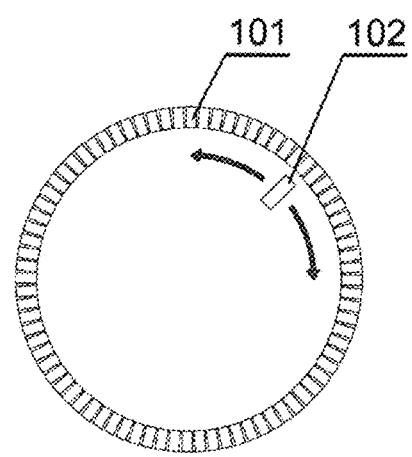
FIG. 3 presents a schematic outline of a strip TOF-PET scanner with a collimated beam of gamma quanta, in longitudinal cross-section.
Figure 4:
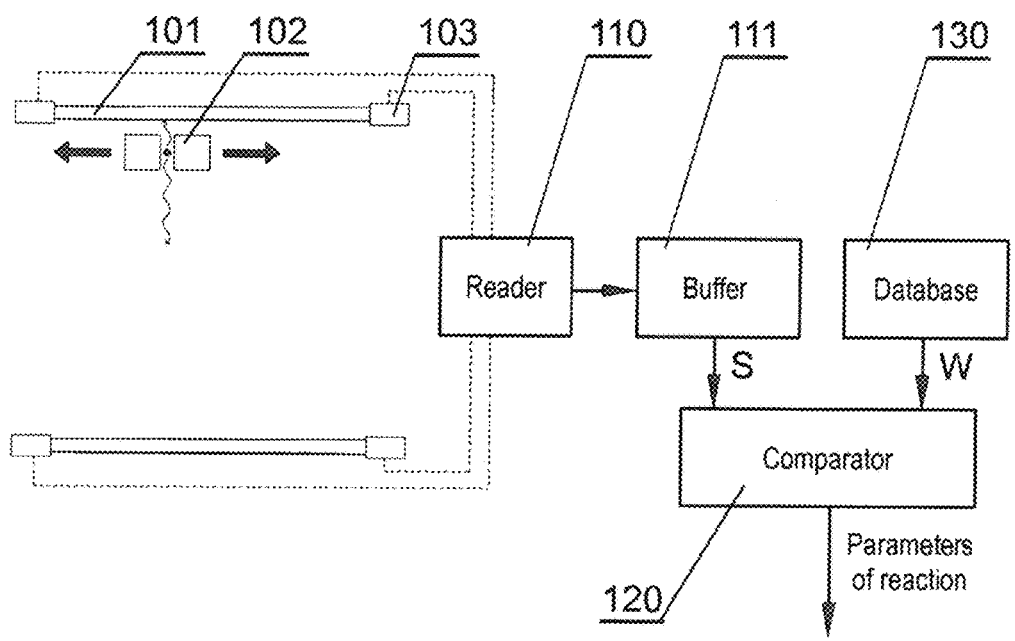
FIG. 4 presents a schematic outline of a strip TOF-PET scanner with a collimated beam of gamma quanta, in transverse cross-section.

Information on the position and time of the annihilation of the positron-electron pair within the object's body is carried by two gamma quanta recorded in scintillating detectors of PET scanners, for example as schematically outlined in FIGS. 3 and 4. The reactions of the gamma quanta within the scintillating detectors 101 result in light pulses which, after reaching the scintillator edges, are transformed into electric pulses by means of photomultipliers 103 or other converters. Signals from photomultipliers are transferred into electronic readout systems (readers) 110 that facilitate the measurement of the signal charges and times of crossing preset voltage thresholds. The measurements of the charges of these pulses as well as of the times of the signals crossing preset reference voltages are used as the basis for determination of the parameters of the reaction of the gamma quantum within the scintillator, such as the position and the time of the incidence of the gamma quantum onto the detector and, as a consequence, the annihilation point along the line of response (LOR) to be subsequently used for reconstruction of tomographic images.

Each signal, when measured, is represented by a point within a generalized measurement space $\Omega p$, with the number of dimensions equal to the number of measurements of times and charges of signals generated at the detectors by a single gamma quantum. Determination of the position and the time of the incidence of the gamma quantum onto the detector consists in comparing the results of the measurement of signals from a particular event with the results of measurements stored within the database 130 in comparator 120 and selecting parameters of the reaction, such as the position and the time of the incidence, that are assigned within database 130 to the pulse, which is the most similar to the signal of the examined event. A measure of similarity of signals may be defined as the distance between the points representing these signals within the $\Omega p$ space. The distance is measured using quantities that take into account the uncertainties in the measurements of times and charges as well as correlations between the results of charge measurement and the times for various reference voltages.

Comparator 120 is used to compare the signal S measured upon acquiring the object's image, represented by point P, with a reference standard signal W from a synchronized database 130, represented by point $B_s$, while the similarity is measured by minimizing the distance between points P and $B_s$ as a function of relative time between both signals. The measured signal S is transmitted to comparator 120 via the signal buffer 111. The signal buffer 111 may transmit data into comparator 120 either in real time or after a delay—for instance immediately after completion of the measurement or after a certain time from the measurement (in such case, buffer 111 acts as a memory for storing the signal S measurement data).

Time corresponding to the gamma quantum reaction generating the pulse represented by point P is taken as the relative time, being the result of minimization of the distance between point P and the synchronized database point $Bs_{fit}$ characterized in that the minimum distance is the lowest for all points within database 130. Finally, the place of the incidence of the gamma quantum onto the detector 101 is determined as the place to which the beam was pointing at the moment the signal represented by point $Bs_{fit}$ in database 130 was recorded. This method for determining the position and time ensures that the difference in times determined for two different detectors 101 that registered the gamma quanta originating from the same annihilation event corresponds to the actual difference in the times of flights (TOF) of these quanta between their origin and the detectors.

In this description, the used indices have the following meanings:

B—a point representing the signal in the reference standard signal database;
$B_s$—a point in the synchronized reference standard signal database;
$B_{sfit}$—a point in the synchronized reference standard signal database that best fits the measured signal.

Let us assume that every device that measures the charge and time of signal's crossing a particular reference voltage or fraction adds one dimension to the generalized measurement space $\Omega p$. Let the number of dimensions within the space be marked by $N_{measurements}=2\times(N_f+N_{sr}+N_{sf}+1)$, where $N_f$ is the number of thresholds in constant fraction discriminators, $N_{sr}$ is the number of time measurements performed using a leading edge discriminator in the rising edge, $N_{sf}$ is the same for the falling edge, and the last dimension (+1) represents the charge measurement. The factor of 2 in front of the parentheses is due to the fact that every detector module records two signals on both ends of the strip. Therefore, the result of the measurement of a single gamma quantum is a point P within an $N_{measurements}$-dimensional space $\Omega p$ wherein the first half of coordinates corresponds to the measurements made on the left side of the strip and the other half of coordinates corresponds to the measurements made on the right side of the strip.

Different coordinates of point P and their reciprocal relationships are to various degrees sensitive to the changes in amplitude, time or shape of the signal. For example, P(i) values for indices "i" in the range of 1 to $N_f$, corresponding to the measurements of time using a constant fraction discriminator are by definition insensitive to pulse amplitude on condition that the shape and obviously the time of the pulse origin remain unchanged. On the other hand, P(i) values for indices "i" in the range of $N_f+1$ to $N_f+N_{sr}$ depend on signal amplitude even if the shape and the time remain unchanged. This is due to the time walk effect. In addition, the difference between the values $P(i)-P(i+N_f+N_{sr}+N_{sf}+1)$, i.e. the difference in times measured at a particular reference voltage for signals at both sides of the strip largely depends on the position where the gamma quantum was recorded. The incidence position is reflected in the difference in the times in which signals arrive to the opposite ends of the strip, i.e. in $P(i)-P(i+N_f+N_{sr}+N_{sf}+1)$, where "i" is in the range from 1 to $N_f+N_{sr}+N_{sf}$ and in the shape of the signal which also depends on the distance between the reaction position and the photomultiplier, translating into the relationship between, for example, P(i)-P(j) where "i" and "j" are in the range of between 1 and $N_f$, and where "i" and "j" are in the range of between $(N_f+1)$ and $(N_f+N_{sr}+N_{sf})$. Therefore, point P provides information on the gamma quantum incidence position, energy being deposited, and the time of incidence. Times P(i) are calculated in reference to the trigger signal time, and therefore only differences P(i)-P(j) between the coordinates of a given point and differences between coordinates that represent measurements from different detection modules may be interpreted as actual time differences.

Points P provide information on the measurements of signals on both sides of the strip. The first $(N_f+N_{sr}+N_{sf}+1)$ coordinates correspond to the signal on one end of the strip while the next $(N_f+N_{sr}+N_{sf}+1)$ coordinates correspond to the signal on the other end of the strip. Indices "i" and "j" correspond to any i-th and any j-th coordinate of point P, i.e. to any pair of coordinates. Analysis may include the time measurements for different voltages or fractions being carried at one end of the strip or one type of measurements being carried out at one end of the strip with the other type of measurements at the other end of the strip. In each case, only the difference is of physical significance, both when measuring times for different voltages for the same signal or when measuring the times for different signals.

A particular event corresponding to the measurement of two annihilation quanta is represented in space $\Omega p$ by two points $P_a$ and $P_b$ that represent the measurements of signals generated by annihilation quanta in detectors a and b:

$$P_a(1) = t_{\_left1\_a},$$
$$\ldots$$
$$P_a(N_f + N_{sr} + N_{sf} + 1) = Q_{\_left\_a}$$
$$\ldots$$
$$P_a(N_{measurements}) = Q_{\_right\_a}$$

where $P_a(1)$ is the first coordinate of $P_a$ representing the time measured at the first threshold on the left, component $(N_f+N_{sr}+N_{sf}+1)$ is the charge of the signal measured on the left side of strip "a", t is the time and Q is the charge.

Whereas the measured result P(i) may be expressed as $$P(i)=t_{crossing\_i}+t_{delay\_i}-t_{trigger},$$

where $t_{trigger}$ has the same value for each i, $t_{crossing\_i}$ is the time after which the signal exceeds the reference voltage in the discriminator corresponding to the i-th dimension within the Ωp space and $t_{delay\_i}$ is a constant subject to calibration and corresponding to the time that has passed until the time of the measurement from the moment at which the signal would have crossed the reference voltage if the measurement was made at the scintillator edge without the delays due to signal transmission within the photomultiplier, cables and electronics.

The results of the measurement of signals from a particular event are compared to the results of measurements stored within the database 130 and parameters assigned within database 130 to the pulse that is most similar to the signal of the particular event are selected as the parameters of the reaction, for example the position and the time of the incidence. Similarity of signals is measured by the distance between these points within the Ωp space. Therefore, in order to determine the position and the time of the reaction of the gamma quantum, for example within strip "a", the synchronized database is searched for a $Bs_{fit}$ point that is closest to point $P_a$.

The measurements, and consequently also the coordinates of points within the Ωp space are burdened by uncertainties that may be correlated with one another. These uncertainties are described by a covariance matrix that has to be determined for each detection module. A matrix inverse to the covariance matrix defines the Ωp space metrics facilitating determination of distances between points within that space. Thus calculated distances that take into account the measurement uncertainties and correlations between the measurements of individual point coordinates are known in the literature as Mahalanobis distances. In general, the measure of distances between points, or the measure of similarity between signals represented by these points, may be defined in numerous ways. For example, the measure of similarity may consist in (i) maximum probability of the compared signals being the same (if similarity is determined using the maximum likelihood method and pre-determined distributions of the probability density for measurement uncertainties);

(ii) minimum chi-square value ($X^2_{min}$) in case of the least squares method; or (iii) minimum Hausdorff distance in case of Hausdorff method, etc.

Figure 1:
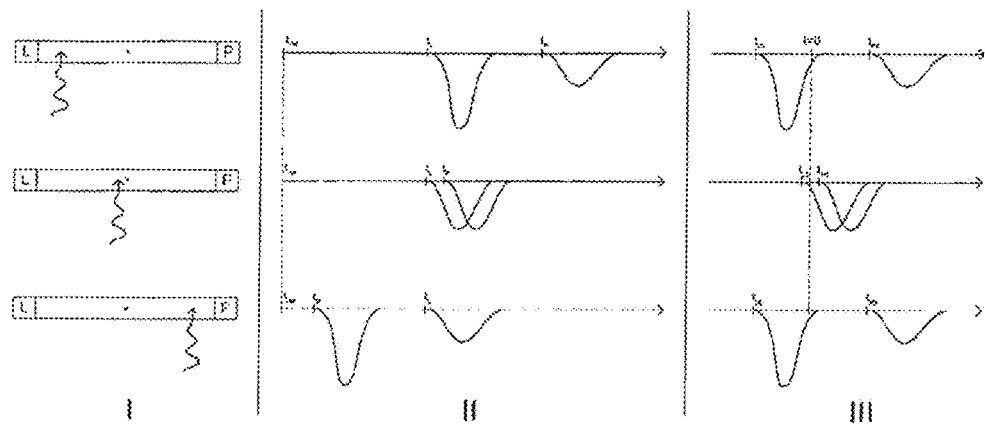
FIG. 1 outlines the generation of a database of reference standard signals and synchronization of signals within the database.

FIG. 1 presents an outline of generation of database signals and synchronization of signals within database 130; Part I presents different positions of incidence of the gamma quanta onto a detector featuring left (L) and right (R) photomultipliers. Part II presents the signals read at respective positions prior to synchronization, while part III presents these signals after synchronization. The set of the Ωp space points B that represent signals that comprise the reconstructional database is not synchronized. The coordinates of points B correspond to the times of signals crossing the threshold voltages at the discriminators, said times being calculated in relation to the time of generation of the signal that triggers the recording of data. In the state of the art PET scanners, the times of pulses that trigger the recording of signals originating from sequential annihilation events are not related to one another. Therefore, the absolute values of the coordinates of points B within the database have no physical meaning. Information on the position of the incidence of the gamma quantum onto the detector is provided only by the difference between the coordinates of point B while no useful information is provided by the differences in times between coordinates of different points within the database. Several example database signals are presented in part II of FIG. 1. The goal of the procedure that synchronizes the signals within the database is to shift the signals in time so that the moment of the reaction of the gamma quantum within the detector would be the starting point of time measurement, as disclosed in Part III of FIG. 1. The time of the reaction of the gamma quantum within the detector relative to the time of arrival of the triggering pulse is determined by the average value $(t_L+t_R)/2$, where $t_L$ is the onset of signal from the left photomultiplier and $t_P$ is the onset of signal from the right photomultiplier. The onsets of the left and the right signals for the measurement represented by point B are determined based on the coordinates of that point by means of fitting of a function that parametrizes the shapes of the signals along the rising edge. Database synchronization consists in shifting point B to point $B_s$ ($B_s(i)=B(i)+t_{synch}$, $i=1,N_{measurements}$), by means of selecting such a $t_{synch}$ value so that after the transformation, $t_{Ls}+t_{Ps}=0$.

The $t_{synch}$ value should be determined separately for each point within the database. For example, for a particular database signal represented by point B, one may calculate the signal onset at the left photomultiplier ($t_L$) and at the right photomultiplier ($t_R$), so as to calculate $t_{synch}$ as:

$$t_{synch}=-(t_L+t_R)/2$$

The database synchronization procedure described above is characteristic for this invention and allows to determine not only the LOR, but also the TOF.

In order to compare the signal from a measurement carried out during the imaging of a object as represented by point P, with the synchronized database signal represented by point $B_s$, one must minimize the distance between points P and $B_s$ by means of variations in relative times between the database points and the imaging data. This means that for example the Mahalanobis distance between points P and $B_s$ is expressed as a function of time $t_{rel}$ used as a fit parameter: Mahalanabis(P+$T_{rel}$, $B_s$), where $T_{rel}=(t_{rel} \ldots, t_{rel})$. For each database point $B_s$, the min(Mahanalobis) value is calculated in relation to $t_{rel}$, and then the $B_{sfit}$ point with the minimum value of min(Mahanalobis(P+$T_{rel}$, $B_{fit}$)) is selected as the database point closest to point P. Ultimately, the position of the incidence of the gamma quantum onto the detector is determined as the position to which the beam was pointing at the time of the measurement of the signal represented by point $Bs_{fit}$, while the time $t_{rel}$ characterized by the minimum Mahalanabis(P+$T_{rel}$, $Bs_{fit}$) value is selected as the time of the reaction of the gamma quantum within the detector. This selection of time is characteristic for this invention and ensures that the difference in times $t_{rel}$ determined for two different detectors that registered the gamma quanta originating from the same annihilation event corresponds to the actual difference in the times of flights (TOF) of these quanta between their origin and the detectors.

Figure 2:
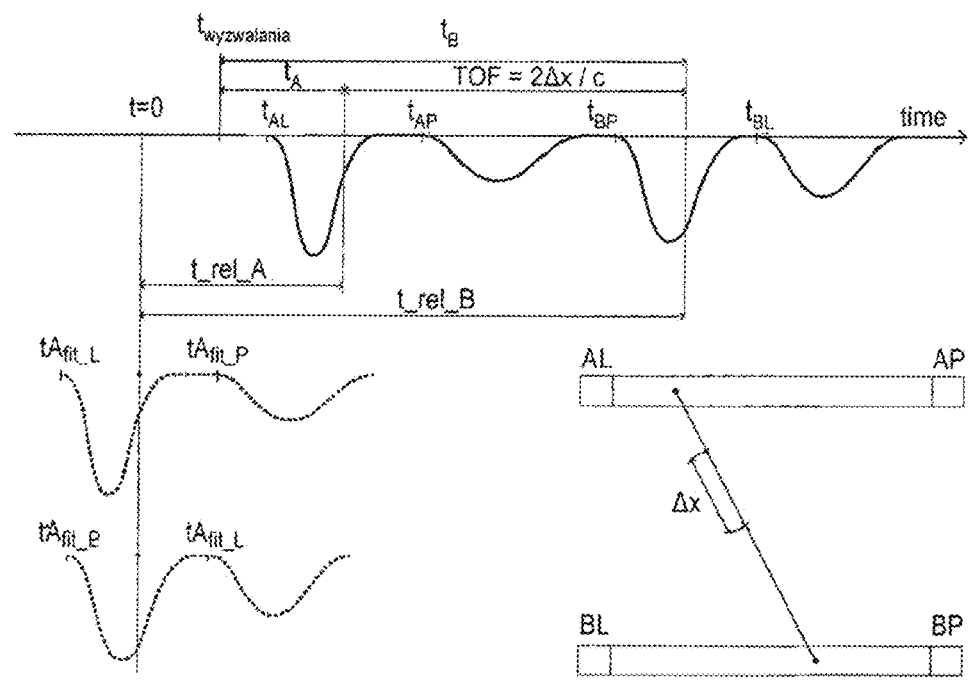
FIG. 2 presents an example TOF reconstruction based on the synchronized database of reference standard signals.

FIG. 2 presents an example TOF reconstruction based on the synchronized database of reference standard signals. Let's make an assumption that gamma quanta were recorded by detectors A and B. In such case, $t_A$, i.e. the time of the reaction of the gamma quantum within detector A relative to the trigger signal time may be calculated as $$t_A=(t_{AL}+t_{AR})/2$$

and, analogously, $$t_B=(t_{BL}t_{BR})/2,$$

where $t_{AL}$ is the time of the signal onset at the left side of detector A relative to the trigger signal time and $t_{AR}$, $t_{BL}$ and $t_{BR}$ are the respective times of the signal onsets at the right side of detector A as well as the left and the right side of detector B. The solid line in FIG. 2 illustrates positions of pulses at the left and right sides of detectors A and B along the time axis for an examplary event with annihilation taking place at a distance of Δx relative to the center of the LOR. The dashed line illustrates pulses from the synchronized database characterized by the best similarity to the pulses recorded at detectors A and B, i.e. pulses identified in the reconstruction procedure. As clearly demonstrated by FIG. 2, using the method to calculate $t_{rel}$ from synchronized database signals, one obtains $$t\_rel\_A = t_A + t_{trigger}$$

and $$t\_rel\_B = t_B + t_{trigger}$$

and thus $$t\_rel\_B - t\_rel\_A = t_B - t_A.$$

Whereas $(t_B-t_A)$ is the difference between the times of arrival of the annihilation quanta at detectors A and B, i.e. TOF, therefore.

$$t\_rel\_B t\_rel\_A = TOF$$

regardless of the time of arrival of the trigger signal.

FIGS. 3 and 4 present a strip TOF-PET scanner with a collimated beam of gamma quanta. The tomographic image is reconstructed on the basis of the determined dataset including lines of response (LOR) and differences in times of flight required for annihilation quanta to reach the detectors (TOF). In order to determine the LOR and the TOF for a particular event, one should determine the position and the time of the reaction of a gamma quantum within the detectors. To this end, a database of signals is generated by means of scanning the strip using a collimated beam of annihilation radiation of a profile lower than the spatial resolution to be achieved. For instance, a beam of the width of 1 mm is generated and moved along the strip while recording measurements and adding tags indicating the irradiation positions to each piece of pulse data. Scanning is performed using the source 102 of annihilation radiation located within a collimator that may rotate around the scanner axis and move along this axis so as to permit irradiation of every point within the detector with a beam of appropriately selected profile. Thus generated and synchronized database of pulses comprises the set of basal points B within the space Ωp.

The method may be used in PET scanners in which the signals are sampled for example within the voltage domain using multi-threshold discriminators.

While the technical solutions presented herein have been depicted, described, and defined with reference to particular preferred embodiment(s), such references and examples of implementation in the foregoing specification do not imply any limitation on the invention. Various modifications and changes may be made thereto without departing from the scope of the technical solutions presented. The presented embodiments are given as example only, and are not exhaustive of the scope of the technical solutions presented herein. Accordingly, the scope of protection is not limited to the preferred embodiments described in the specification, but is only limited by the claims that follow.

The invention claimed is:

1. A method for reconstructing tomographic images, the method comprising determining reaction parameters of a gamma quantum within a scintillation detector of a PET scanner for a signal measured by a scintillator, which is transformed in at least one photomultiplier into an electric measured signal (S), the method comprising the steps of:

obtaining an access to a database comprising reference standard signals (W) and the reaction parameters assigned to the reference standard signals (W);

wherein the measured signal (S) and the reference standard signals (W) are represented by points (P) within a generalized measurement space (Ωp) having a number of dimensions ($N_{measurements}$) being equal to a total number of time measurements performed for that gamma quantum;

comparing the measured signal (S) to the reference standard signals (W) and selecting the reference standard signal (W) that best fits the measured signal (S), wherein the reference standard signal (W) that best fits measured signal (S) is selected by minimizing distances between the points (P) representing the measured signal (S) and the reference standard signal (W) within the generalized measurement space (Ωp) as a function of the relative times between the compared measured signal (S) and reference standard signal (W);

assigning, to the signal measured by the scintillator corresponding to the measured signal (S), the reaction parameters assigned to the selected best-fitting reference standard signal (W);

wherein the reaction parameters comprise a position and a time of incidence of the gamma quantum onto the scintillation detector;

reconstructing the tomographic image based on the reaction parameters assigned to the signal measured by the scintillator corresponding to the measured signal (S).

2. The method according to claim 1, wherein coordinates of the points (P) are ordered and correspond to crossing times when the signals (S, W) cross threshold voltages, measured using discriminators and/or amplitudes or charges of the signals (S, W).

3. The method according to claim 1, wherein the generalized measurement space (Ωp) comprises dimensions of time measurements ($N_f$) carried out by means of a constant fraction discriminator for the rising edge of the signal (S, W), as well as dimensions of time measurements for the rising edge ($N_{sr}$) and for the falling edge ($N_{sf}$) of the signal (S, W) measured by a leading edge discriminator.

4. The method according to claim 1, wherein a total of $N_f + N_{sr} + N_{sf}$ time measurements are carried out with respect to a trigger signal.

5. The method according to claim 1, wherein the reference standard signals (W) are generated using a collimated beam of gamma quanta.

6. The method according to claim 5, wherein each of the reference standard signals (W) in the database is assigned information on a position of incidence of the collimated beam of gamma quanta onto the scintillation detector.

7. The method according to claim 1, wherein the reference standard signals (W) contained in the database are synchronized such that for each of the reference standard signals (W) the time corresponding to the reaction of the gamma quantum within the scintillation detector is the same, preferably equal to zero.

8. The method according to claim 7, further comprising determining a time of flight (TOF) as a difference in time between the measured signals (S) and the best-fitting reference standard signals (W).

9. A system for reconstructing tomographic image, comprising determining reaction parameters of a gamma quantum within a scintillation detector of a PET scanner for a signal measured by a scintillator, which is transformed in at least one photomultiplier into an electric measured signal (S), wherein the system comprises:
- a database comprising reference standard signals (W) and the reaction parameters assigned to the reference standard signals (W), wherein the measured signal (S) and the reference standard signals (W) are represented by points (P) within a generalized measurement space ($\Omega p$) having a number of dimensions ($N_{measurements}$) being equal to a total number of time measurement performed for that gamma quantum;
- a comparator configured to;
  - compare the measured signal (S) with the reference standard signals (W);
  - select the reference standard signal that best fits the measured signal (S), wherein the reference standard signal (W) that best fits the measured signal (S) is selected by minimizing distances between the points (P) representing the measured signal (S) and the reference standard signal (W) within the generalized measurement space ($\Omega p$) as a function of the relative times between the compared measured signal (S) and reference standard signal (W); and
  - assign, to the signal measured by the scintillator corresponding to the measured signal (S), the reaction parameters assigned to the selected best-fitting reference standard signal (W);
- wherein the reaction parameters comprise a position and a time of incidence of the gamma quantum onto the scintillation detector; and
- wherein the system is configured to reconstruct the tomographic image based on the reaction parameters assigned to the signal measured by the scintillator corresponding to the measured signal (S).

10. The method according to claim 1, further comprising determining a time of flight (TOF) as a difference in time between the measured signals (S) and the best-fitting reference standard signals (W).

* * * * *